(12) United States Patent
Kurakazu et al.

(10) Patent No.: US 10,351,811 B2
(45) Date of Patent: Jul. 16, 2019

(54) CELL CULTURE CONTAINER

(71) Applicant: SINFONIA TECHNOLOGY CO., LT, Tokyo (JP)

(72) Inventors: Tomoaki Kurakazu, Stevenage (GB); Yasuhiro Oshima, Stevenage (GB); Yoshio Kimura, Koshi (JP); Kenichi Kagawa, Tokyo (JP); Shinichi Gomi, Tokyo (JP); Shigenori Ozaki, Tokyo (JP)

(73) Assignee: SINFONIA TECHNOLOGY CO., LTD., Tokyo (JP)

( * ) Notice: Subject to any disclaimer, the term of this patent is extended or adjusted under 35 U.S.C. 154(b) by 238 days.

(21) Appl. No.: 15/240,284

(22) Filed: Aug. 18, 2016

(65) Prior Publication Data

US 2016/0355773 A1 Dec. 8, 2016

Related U.S. Application Data

(63) Continuation of application No. PCT/JP2015/054172, filed on Feb. 16, 2015.

(30) Foreign Application Priority Data

Feb. 20, 2014 (JP) ................................. 2014-030515

(51) Int. Cl.
*C12M 1/00* (2006.01)
*C12M 1/04* (2006.01)
(Continued)

(52) U.S. Cl.
CPC ............ *C12M 23/12* (2013.01); *C12M 23/04* (2013.01); *C12M 23/20* (2013.01); *C12M 23/24* (2013.01);
(Continued)

(58) Field of Classification Search
CPC ...... C12M 23/12; C12M 23/20; C12M 23/04; C12M 23/24; C12M 25/00; C12M 25/06; C12M 29/10
See application file for complete search history.

(56) References Cited

U.S. PATENT DOCUMENTS 6,479,252 B1 * 11/2002 Barbera-Guillem ........................ C12M 23/10 435/173.1
2002/0086329 A1 * 7/2002 Shvets .................. B01L 3/5027 435/7.1

(Continued)

FOREIGN PATENT DOCUMENTS

EP 2230014 A1 9/2010
JP 2004-173681 A 6/2004
(Continued)

OTHER PUBLICATIONS

ISR issued in corresponding international application No. PCT/JP2015/054172 dated May 12, 2015.

*Primary Examiner* — Michael L Hobbs
(74) *Attorney, Agent, or Firm* — Nath, Goldberg & Meyer; Jerald L. Meyer

(57) ABSTRACT

A cell culture container characterized by being equipped with a container main body and a flat plate attached onto one surface of the container main body, wherein the container main body is equipped with an inflow port through which a liquid can flow into the container main body, a passage through which the liquid flowing into the container main body from the inflow port can pass, and an outflow port through which the liquid passing through the passage can flow out from the container main body, and wherein, on the bottom surface of the passage, multiple cell-seeding areas in (Continued)

which cells passing through the passage can be seeded are arranged side by side along the passage.

12 Claims, 12 Drawing Sheets

(51) Int. Cl.
  *C12M 1/32* (2006.01)
  *C12M 1/12* (2006.01)
(52) U.S. Cl.
  CPC ............ *C12M 25/00* (2013.01); *C12M 25/06* (2013.01); *C12M 29/10* (2013.01)

(56) References Cited

U.S. PATENT DOCUMENTS

| | | | |
|---|---|---|---|
| 2009/0181158 A1* | 7/2009 | Ikeya | C12M 23/12 427/2.13 |
| 2010/0003745 A1* | 1/2010 | Takahashi | C12M 23/58 435/289.1 |

FOREIGN PATENT DOCUMENTS

| | | | |
|---|---|---|---|
| JP | 2005-080607 A | 3/2005 | |
| JP | 2006-094783 A | 4/2006 | |
| JP | 2006-122012 A | 5/2006 | |
| JP | 2007-097407 A | 4/2007 | |
| JP | 2010-011747 A | 1/2010 | |
| JP | 2010-063429 A | 3/2010 | |
| WO | 2011/083768 A1 | 7/2011 | |
| WO | 2012/115276 A1 | 8/2012 | |

\* cited by examiner

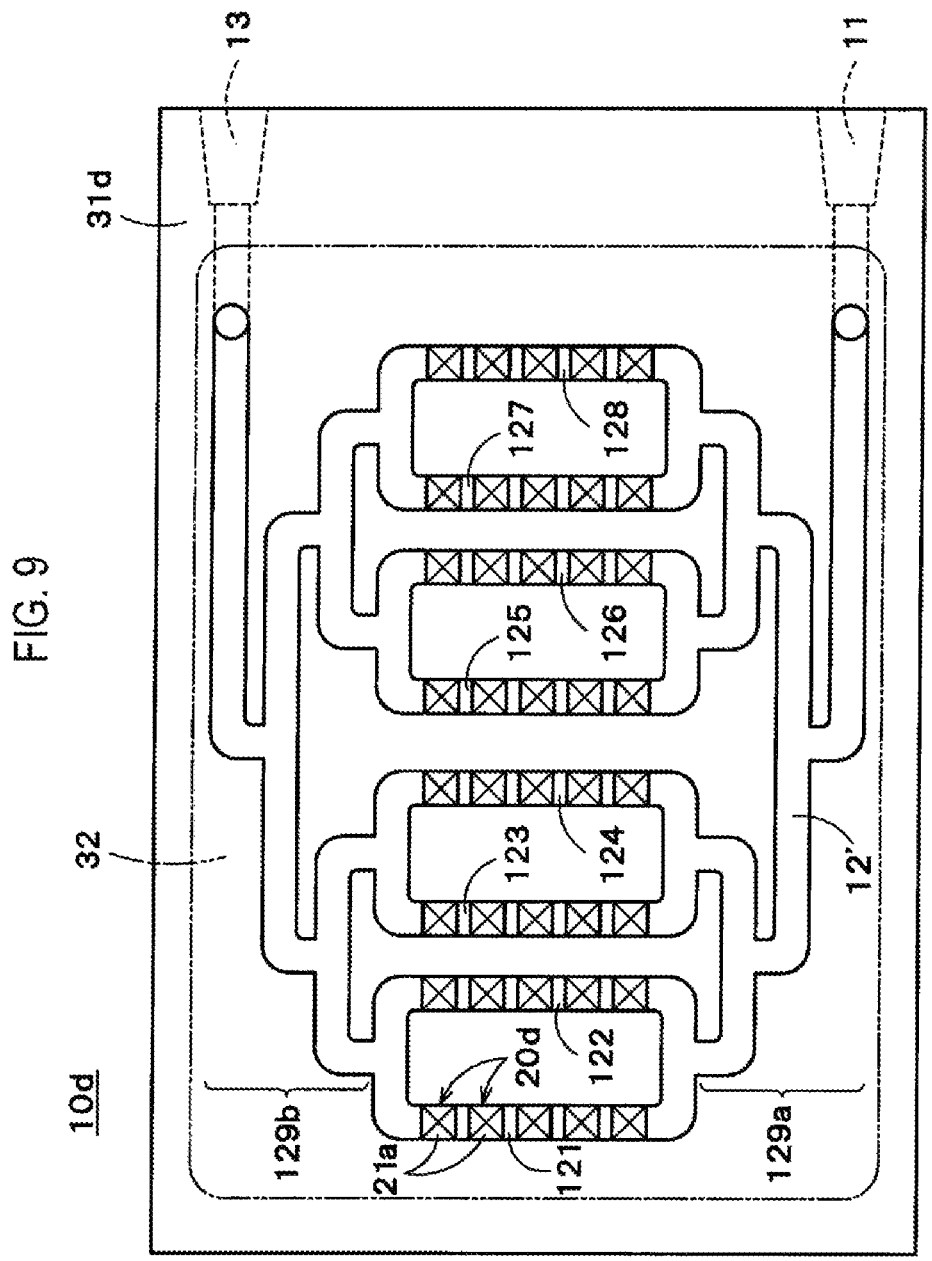

CELL CULTURE CONTAINER

CROSS-REFERENCE TO RELATED APPLICATION

This application is a Continuation Application of PCT International Application No. PCT/JP2015/054172, filed on Feb. 16, 2015, which claimed the benefit of Japan Patent Application No. 2014-030515, filed on Feb. 20, 2014, the entire content of each of which is hereby incorporated by reference.

TECHNICAL FIELD

The present invention relates to a cell culture container.

BACKGROUND

In recent years, research and development of regenerative medicine for artificially producing target tissues or organs through cell culture are underway. A cell culture facility that meets predetermined criteria, for example, a GMP (Good Manufacturing Practice), is used to perform a culture operation of cells.

In the related art, an open-type culture container such as a dish or flask has been used to culture induced pluripotent stem cells (hereinafter referred to as iPS cells) or embryonic stem cells (hereinafter referred to as ES cells). A liquid such as a cell suspension, a culture media or the like is introduced into the container, or a liquid or a cell is recovered from the container, by pipetting which is carried out with the hand of a man. In the culture of iPS cells, ES cells or the like, it is necessary to carry out the culture by forming a colony having a predetermined size. The colony which has grown larger by the culture is subcultured by crushing a cell clump into an appropriate size by virtue of pipetting. However, in the open-type culture container, an internal space of the container communicates with an ambient air at the time of opening a lid. Thus, there is a risk that the container is contaminated by a bacteria or a virus introduced from the outside.

There is known a closed-type culture container which can compensate the defects of the open-type culture container (see, e.g., U.S. Pat. No. 6,479,252 and Japanese Patent Application Publication No. 2010-11747). In the closed-type culture container, there is provided an access port that permits access from the outside to the internal space of the container. A syringe is inserted into the access port at the time of injection or discharge of a liquid. This reduces a risk of contamination from the outside.

SUMMARY

However, in the closed-type cell culture container, culture is carried out in a state in which cells adhere to a continuous culture surface formed on one surface within a closed container. Thus, it is impossible to directly gain access to the cells by virtue of pipetting or the like. For that reason, it is impossible to make uniform the size of cell clumps to be cultured. It is also impossible to control culture positions of cells.

In view of the problems noted above, the present invention has been made to effectively solve the problems. It is an object of the present invention to provide a closed-type cell culture container for simultaneously culturing a plurality of cell clumps, which is capable of making the size of the cell clumps to be cultured uniform and capable of controlling culture positions of cells.

The present invention is directed to a cell culture container, including: a container main body; and a flat plate attached to one surface of the container main body, wherein the container main body includes a an inflow port through which a liquid flows into the container main body, a passage through which the liquid flowing into the container main body from the inflow port passes, and an outflow port through which the liquid passing through the passage flows out from the container main body, and a plurality of cell-seeding areas, in which cells passing through the passage are seeded, is provided on a bottom surface of the passage and is arranged side by side along the passage.

Preferably, the cell-seeding areas are provided at regular intervals along the passage.

Preferably, the passage includes a serpentine portion.

Preferably, the passage includes a branching section in which the passage is branched into a plurality of passage components and a merging section in which the passage components are merged.

Preferably, cavities are formed on the bottom surface of the passage in a concentric relationship with the cell-seeding areas.

In this case, preferably, the cavities have a pyramidal shape or a conical shape.

Alternatively, each of the cavities includes a flat bottom portion.

Furthermore, in the case where the cavities are formed on the bottom surface of the passage, an extracellular matrix (ECM) is coated on a portion of the flat plate which faces the cavities.

Alternatively, in the case where each of the cavities includes a flat bottom portion, an extracellular matrix (ECM) may be coated inside the cavities and may not be coated outside the cavities.

Alternatively, the bottom surface of the passage may be flat and an extracellular matrix (ECM) may be coated inside the cell-seeding areas and may not be coated outside the cell-seeding areas.

Preferably, an outer surface roughness of the cell-seeding areas is larger than an inner surface roughness of the cell-seeding areas.

Preferably, the bottom surface of the passage and the flat plate have optical transparency.

Preferably, the flat plate has gas permeability.

BRIEF DESCRIPTION OF THE DRAWINGS

FIG. 9 is a schematic plane view illustrating a cell culture container according to a fourth embodiment of the present invention.

DETAILED DESCRIPTION

Figure 1A:
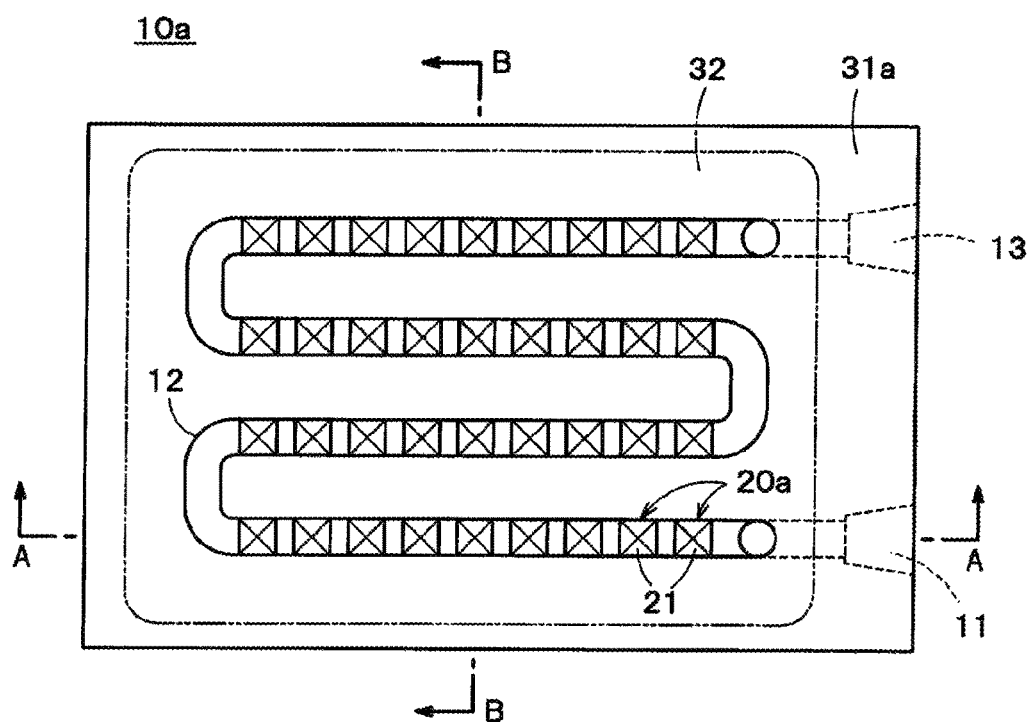
FIG. 1A is a schematic plane view illustrating a cell culture container according to a first embodiment of the present invention.

Embodiments of the present invention will now be described in detail with reference to the accompanying drawings. In the drawings attached to the subject specification, for the sake of the ease of understanding of illustration, the reduced scale and the aspect ratio are appropriately changed and exaggerated from the actual ones.

First Embodiment

Figure 1B:
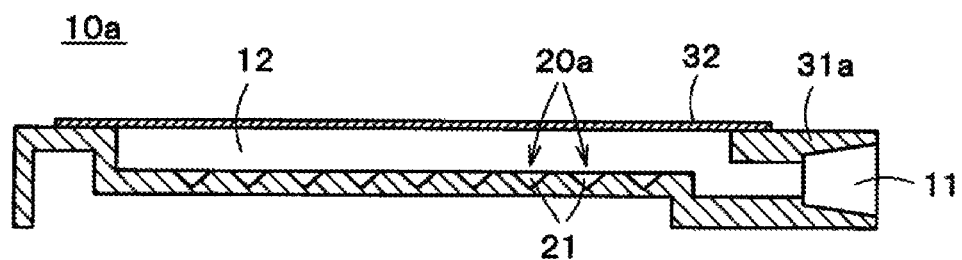
FIG. 1B is a sectional view of the cell culture container taken along line A-A in FIG. 1A.
Figure 1C:
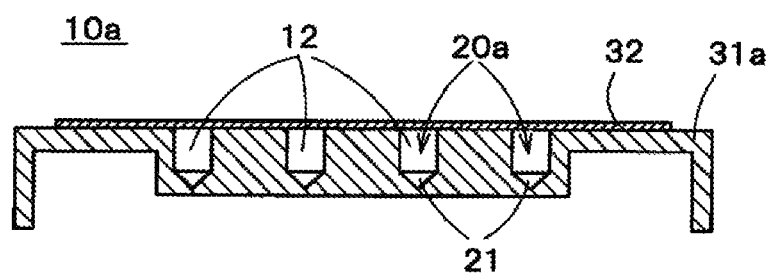
FIG. 1C is a sectional view of the cell culture container taken along line B-B in FIG. 1A.

FIG. 1A is a schematic plane view illustrating a cell culture container according to a first embodiment of the present invention. FIG. 1B is a sectional view of the cell culture container taken along line A-A in FIG. 1A. FIG. 1C is a sectional view of the cell culture container taken along line B-B in FIG. 1A.

A cell culture container 10a of the present embodiment can be used to culture different adhesive (adherent) cells including pluripotent stem cells such as iPS cells, ES cells or the like, chondrocytes such as bone marrow stromal cells (MSC) or the like, dendritic cells, and so forth. In the present embodiment, descriptions will be made under the assumption that the cell culture container 10a is mainly used to culture iPS cells. However, this is nothing more than one example.

As illustrated in FIGS. 1A to 1C, the cell culture container 10a according to the present embodiment includes a container main body 31a and a flat plate 32 attached onto one surface of the container main body 31a. A light-transmitting resin, for example, polystyrene, is used as a material of the container main body 31a and the flat plate 32. Since the container main body 31a and the flat plate 32 have optical transparency, it is easy to optically observe the cells in culture from the outside.

In the present embodiment, as illustrated in FIG. 1A, the container main body 31a has a substantially rectangular shape in a plane view. Specifically, the container main body 31a has, for example, a longitudinal dimension of 130 mm, a transverse dimension of 85 mm and a height dimension of 10 mm.

As illustrated in FIG. 1A, the container main body 31a includes an inflow port 11 through which a liquid (a cell-dispersed liquid, a culture solution, a release agent, a phosphate-buffered saline (PBS) or the like) flows into the container main body 31a, a passage 12 through which the liquid flowing into the container main body 31a from the inflow port 11 passes, and an outflow port 13 through which the liquid passing through the passage 12 flows out from the container main body 31a. The inflow port 11, the passage 12 and the outflow port 13 are integrally formed by, for example, injection molding.

As illustrated in FIGS. 1B and 1C, the passage 12 of the container main body 31a is formed in a groove shape on one surface of the container main body 31a to which the flat plate 32 is attached. It is preferred that the diameter of the passage 12 (namely, the depth and width of the groove) is 2 mm or more. If the growth limit size of a colony of iPS cells is from 2 mm to 3 mm and if the diameter of the passage 12 is smaller than 2 mm, the growth of the colony of the iPS cells is limited by the passage 12. Furthermore, it is preferred that the diameter of the passage 12 is 4 mm or less. If the diameter of the passage 12 is larger than 4 mm, the effect of the orientation of a liquid flow being limited by the passage 12 is weakened and a turbulent flow is likely to occur. It is preferred that the diameter of the passage 12 is from 2 mm to 4 mm.

Furthermore, as illustrated in FIG. 1A, the passage 12 of the container main body 31a includes a serpentine portion in a plane view, namely a portion in which linear sections and folded sections are alternately connected to each other. This makes it possible to extend the total length of the passage 12 without increasing the size of the container main body 31a. The ratio of the width, height and length of the passage 12 (the aspect ratio) may be set such that, for example, the width:the height:the length is equal to 3:4:60 to 1800.

As illustrated in FIG. 1A, on the bottom surface of the passage 12, multiple cell-seeding areas 20a, in which cells passing through the passage 12 are seeded, are arranged side by side along the passage 12. As set forth above, the growth limit size of the colony of the iPS cells is from 2 mm to 3 mm. Therefore, it is preferred that the pitch (the center interval) of the cell-seeding areas 20a is set to fall within a range of 2 mm to 3 mm in conformity with the growth limit size so that the ends of the colony do not overlap with each other. This makes it possible to secure a wide seeding area without allowing the adjoining colony ends to be bonded to each other. A minimum boundary may be left between two adjoining cell-seeding areas 20a. The gap between the edges of two adjoining cell-seeding areas 20a may be, for example, 2 mm or less.

While not illustrated in the drawings, it is preferred that the outer surface roughness of the cell-seeding areas 20a is larger than the inner surface roughness of the cell-seeding areas 20a. For example, the inner surface roughness of the cell-seeding areas 20a may be Ra 0.2 or less and the outer surface roughness of the cell-seeding areas 20a may be Ra 0.8 or less. The term "Ra" used herein refers to an arithmetic average roughness which is stipulated in JISB0601. The difference in the surface roughness can be realized by, for example, adjusting the surface roughness of a mold used in injection-molding the container main body 31a. As the outer surface roughness of the cell-seeding areas 20a grows larger, the cells are harder to adhere to the outside of the cell-seeding areas 20a.

In the present embodiment, as illustrated in FIGS. 1B and 1C, cavities 21 are formed on the bottom surface of the passage 12 in a concentric relationship with the cell-seeding areas 20a. In the illustrated example, the cavities 21 have a quadrangular pyramid shape. However, the shape of the cavities 21 is not limited thereto. The cavities 21 may have an n-angular pyramid shape (where n is a natural number of 3 or 5 or more) or a conical shape.

It is preferred that the apex angle of the cavities 21 is 90 degrees or less. If the apex angle of the cavities 21 is larger than 90 degrees, the cells are hard to slide down along the slant surfaces of the cavities 21. Furthermore, it is preferred that the apex angle of the cavities 21 is 30 degrees or more. If the apex angle of the cavities 21 is smaller than 30 degrees, the cells are hard to drop from the inside of the cavities 21 when the container is inverted as will be described later. It is preferred that the apex angle of the cavities 21 is from 30 degrees to 90 degrees.

The inflow port 11 and the outflow port 13 of the container main body 31a are provided on the same surface of the container main body 31a. The inflow port 11 communicates with one end of the passage 12. The outflow port 13 communicates with the other end of the passage 12. While not illustrated in the drawings, a rubber plug with a slit into which a distal end of a syringe can be inserted, an elastic membrane into which a syringe needle can be stabbed, or a structure provided with a medical-purpose opening/closing valve such as a Luer lock or the like, is installed in each of the inflow port 11 and the outflow port 13. This makes it possible to reduce the risk of contamination from the outside at the time of injection and recovery of a liquid.

The flat plate 32 of the present embodiment is formed thin so as to have proper gas permeability. The thickness of the flat plate 32 may be, for example, from 50 μm to 200 μm. This makes it easy to supply a gas such as an oxygen gas or the like to the cells in culture. In the case of culturing anaerobic cells, it is preferred that the flat plate 32 has gas impermeability. In this case, the thickness of the flat plate 32 may be, for example, from 2000 μm to 3000 μm.

The flat plate 32 is opposed to and disposed on one surface of the container main body 31a, on which the passage 12 is formed, so as to cover the entirety of a ceiling of the passage 12. The flat plate 32 is attached to and fixedly supported by the outer portion of the passage 12 (namely, the tip region of the wall that defines the passage 12). In the present embodiment, the flat plate 32 is bonded to the outer portion of the passage 12 by an adhesive agent. However, the fixing method is not limited to the adhesive bonding but may be, for example, heat fusion bonding or ultrasonic welding. Since the flat plate 32 is fixedly supported by the outer portion of the passage 12, it is possible to suppress the bending of the flat plate 32.

Next, one example of a use method of the cell culture container 10a according to the present embodiment will be described with reference to FIGS. 2A to 2E.

Figure 2A:
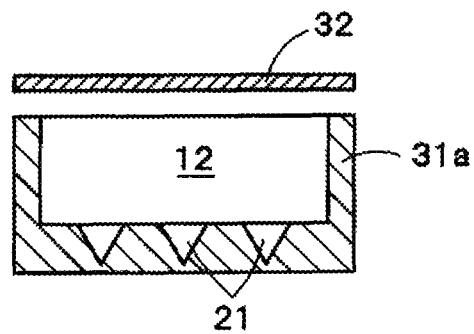
FIG. 2A is a schematic view for explaining one example of a use method of the cell culture container according to the first embodiment of the present invention.

First, as illustrated in FIG. 2A, the surface of the container main body 31a, on which the passage 12 is formed and to which the flat plate 32 is not yet attached, is processed by $O_2$ plasma. Specifically, for example, an $O_2$ gas supplied at a flow rate of 40 mL/min is converted to $O_2$ plasma by electric power of 27 kW. The surface of the container main body 31a, on which the passage 12 is formed, is exposed to the $O_2$ plasma for 5 minutes.

Then, a cell non-adhesive coating solution is coated on the passage 12 of the container main body 31a. Specifically, for example, 10 mL of the cell non-adhesive coating solution is allowed to flow into the passage 12 and is left at rest for 2 hours at 37° C. Thereafter, the cell non-adhesive coating solution is allowed to flow out from the passage 12. The passage 12 is cleaned with sterile water.

Figure 2B:
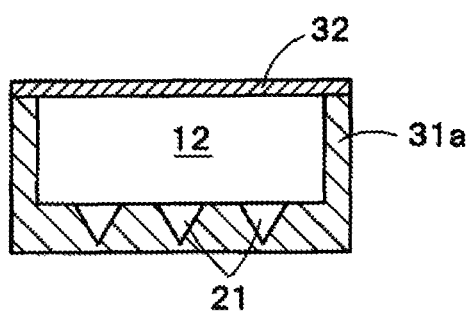
FIG. 2B is a schematic view for explaining one example of a use method of the cell culture container according to the first embodiment of the present invention.

Subsequently, as illustrated in FIG. 2B, the flat plate 32 is attached to one surface of the container main body 31a, on which the passage 12 is formed. Specifically, for example, an adhesive agent (not shown) is coated on the outer portion of the passage 12. Thereafter, the flat plate 32 is opposed to and placed on one surface of the container main body 31a so as to cover the entirety of the ceiling of the passage 12 and is bonded to one surface of the container main body 31a by an adhesive agent. Then, the adhesive agent is solidified at 40° C. for 16 hours by a drier.

Then, PBS is allowed to flow from the inflow port 11 into the passage 12. The passage 12 is filled with the PBS. Thus, air bubbles are removed from the passage 12. Thereafter, the culture container 10a is left at rest in such a posture that the container main body 31a is positioned under the flat plate 32.

Figure 2C:
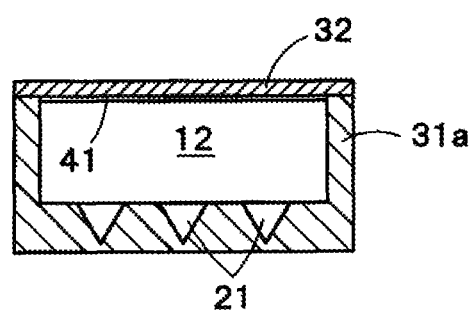
FIG. 2C is a schematic view for explaining one example of a use method of the cell culture container according to the first embodiment of the present invention.

Subsequently, as illustrated in FIG. 2C, an extracellular matrix (hereinafter referred to as ECM) 41 is coated on the region of the flat plate 32 that faces the cavities 21. Specifically, for example, 25 mL of the ECM (e.g., Vitronectin XF made by Stem Cell Technologies, Inc.) is allowed to flow from the inflow port 11 into the passage 12 in a state in which a 1 mL air plug is inserted into the inflow port 11. The PBS existing within the passage 12 is swept away by the ECM and is caused to flow out from the outflow port 13. In this state, the cell culture container 10a is left at rest for 1 hour. Thus, the ECM 41 adheres to the portion of the passage 12 on which the cell non-adhesive coating solution is not coated, namely the entire region of the flat plate 32 corresponding to the ceiling surface of the passage 12.

Figure 2D:
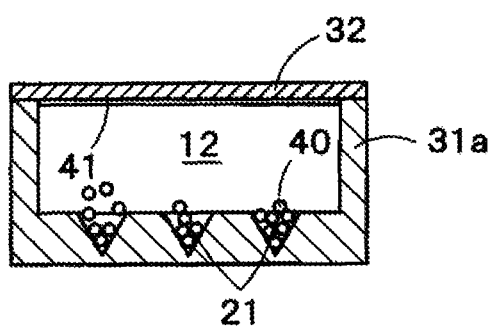
FIG. 2D is a schematic view for explaining one example of a use method of the cell culture container according to the first embodiment of the present invention.

Subsequently, in a cell seeding process, as illustrated in FIG. 2D, 25 mL of a cell suspension in which cells 40 are dispersed (for example, a cell suspension in which iPS cells are dispersed) is allowed to flow from the inflow port 11 into the passage 12 at a flow rate of, e.g., 10 mL/min to 20 mL/min a state in which a 1 mL air plug is inserted into the inflow port 11. The cells 40 in the cell suspension may be dispersed in the form of a single cell or in the forth of a cell clump. The ECM not adhering the flat plate 32 is swept away by the cell suspension and is caused to flow out from the outflow port 13.

In the present embodiment, the orientation of the liquid flow from the inflow port 11 to the outflow port 13 is limited by the passage 12. Therefore, within the passage 12, the moving direction of individual liquid molecules constituting the liquid is aligned parallel to the passage 12. That is to say, occurrence of a turbulent flow between the inflow port 11 and the outflow port 13 is suppressed. Thus, occurrence of unevenness of a cell density in the cell suspension is suppressed. The cells 40 are controlled to fall (precipitate) onto the bottom surface of the passage 12 at a practically-permissible uniform density.

Furthermore, in the present embodiment, the outer surface roughness of the cell-seeding areas 20a is relatively large. Therefore, adhesion of the cells to the outside of the cell-seeding areas 20a is suppressed.

Subsequently, vibration (of a frequency of, e.g., 180 Hz) is applied to the entirety of the cell culture container 10a for 30 minutes. Thus, the cells 40 falling onto the outside of the cavities 21 of the bottom surface of the passage 12 are guided into the cavities 21. That is to say, the cells 40 are effectively condensed inside the cell-seeding areas 20a. Furthermore, since the cavities 21 of the present embodiment have a pyramidal shape or a conical shape, the cells 40 falling into the cavities 21 are slid down along the slant surfaces of the pyramidal or conical cavities 21. Thus, the cells 40 can be condensed at a high density around the apex portions of the cavities 21. Specifically, for example, about 100 to 1000 cells 40 are condensed within each of the cavities 21.

Figure 2E:
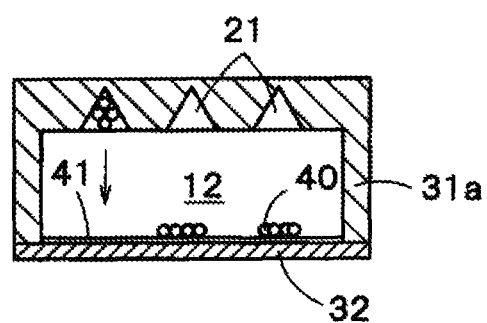
FIG. 2E is a schematic view for explaining one example of a use method of the cell culture container according to the first embodiment of the present invention.

Subsequently, as illustrated in FIG. 2E, the cell culture container 10a is inverted upside down after it is left at rest. Thus, the cells 40 condensed inside the cavities 21 fall onto the portions of the flat plate 32 which face the cavities 21.

Since the ECM 41 is coated on the portions of the flat plate 32 which face the cavities 21, the cells 40 falling onto the flat plate 32 can be cultured in situ using the ECM 41 as a scaffold.

Subsequently, after the cell culture container 10a is left at rest for 48 hours, the cultured cells 40 are optically observed from the outside.

Then, in a medium exchange process, a medium (e.g., ReproFF2 made by Reprocell, Inc.) is allowed to flow from the inflow port 11 into the passage 12 at a flow rate of, for example, 10 mL/min to 20 mL/min. The old medium existing within the passage 12 is swept away by the new medium and is allowed to flow out from the outflow port 13. In the present embodiment, a flow moving along the passage 12 is formed within the passage 12. For that reason, the new medium is hardly mixed with the old medium. Since the old medium is swept away by the new medium, it is possible to easily and effectively exchange the old medium with the new medium without continuously supplying the new medium.

Then, after the cell culture container 10a is left at rest for 48 hours, the cultured cells 40 are optically observed from the outside.

Subsequently, in a medium exchange process, a medium (e.g., ReproFF2 made by Reprocell, Inc.) is allowed to flow from the inflow port 11 into the passage 12 at a flow rate of, for example, 10 mL/min to 20 mL/min. The old medium existing within the passage 12 is swept away by the new medium and is allowed to flow out from the outflow port 13.

Thereafter, the cell culture container 10a is further left at rest for 48 hours. Thus, the cells 40 are cultured until the number of cells 40 becomes equal to 3000 to 20000 per one colony.

Subsequently, in a cell recovery process, a release agent (for example, TrypLE Select made by Life technologies, Inc.) is allowed to flow from the inflow port 11 into the passage 12 at a flow rate of, for example, 10 mL/min to 20 mL/min. The old medium existing within the passage 12 is swept away by the release agent and is allowed to flow out from the outflow port 13. The colonies of the cells 40 cultured on the flat plate 32 are separated from the ECM 41 by the release agent.

Thereafter, a medium (e.g., ReproFF2 made by Reprocell, Inc.) is allowed to flow from the inflow port 11 into the passage 12 at a flow rate of, for example, 10 mL/min to 20 mL/min. The colonies of the cultured cells 40 separated from the ECM 41 are swept away by the new medium and are allowed to flow out (recovered) from the outflow port 13. In the present embodiment, a flow moving along the passage 12 is formed within the passage 12. Therefore, a shear stress is applied uniformly to the bottom surface of the passage 12. This reduces missing of the cultured cells 40.

According to the present embodiment described above, the cells 40 existing in the liquid passing through the passage 12 are seeded inside the cell-seeding areas 20a arranged side by side along the passage 12. It is therefore possible to make uniform the size of the cultured cell clumps and to control the culture position to a predetermined position corresponding to each of the cell-seeding areas 20a.

Furthermore, according to the present embodiment, the orientation of the liquid flow from the inflow port 11 to the outflow port 13 is limited by the passage 12. Therefore, within the passage the moving direction of individual liquid molecules constituting the liquid is aligned parallel to the passage 12. That is to say, occurrence of a turbulent flow between the inflow port 11 and the outflow port 13 is suppressed. Thus, occurrence of unevenness of a cell density in the liquid is suppressed at the time of seeding the cells. The size of the cultured cell clumps is made uniform. Furthermore, the new medium is hardly mixed with the old medium at the time of exchanging the media. Since the old medium is swept away by the new medium, it is possible to easily remove the old medium without continuously supplying the new medium. This makes it possible to effectively exchange the media (That is to say, a loss does not occur at the time of exchanging liquids). In addition, a shear stress is applied uniformly to the bottom surface of the passage 12 at the time of recovering the cells. This reduces missing of the cultured cells 40.

Furthermore, according to the present embodiment, the cell-seeding areas 20a are provided at regular intervals along the passage 12. It is therefore possible to control the culture positions of the cells 40 so that the culture positions are disposed at regular intervals along the passage 12. Thus, the density of the cells in culture becomes uniform along the passage 12. This makes it easy to manage the quality of the cultured cells 40.

Furthermore, according to the present embodiment, the passage 12 has a serpentine portion. It is therefore possible to extend the total length of the passage 12 without increasing the size of the container main body 31*a*. This makes it possible to increase the number of culture positions without enlarging the width of the passage 12. Consequently, a larger number of cell clumps can be simultaneously cultured in one container 10*a*.

Furthermore, according to the present embodiment, the cavities 21 are formed on the bottom surface of the passage 12 in a concentric relationship with the cell-seeding areas 20*a*. Therefore, as the container 10*a* is vibrated, the cells 40 falling to the outside of the cavities 21 are guided into the cavities 21. That is to say, the cells 40 can be effectively seeded within the cell-seeding areas 20*a*.

Furthermore, according to the present embodiment, the outer surface roughness of the cell-seeding areas 20*a* is larger than the inner surface roughness of the cell-seeding areas 20*a*. Therefore, adhesion of the cells to the outside of the cell-seeding areas 20*a* is suppressed. Accordingly, the cells existing in the liquid can be effectively seeded inside the cell-seeding areas 20*a*.

Furthermore, according to the present embodiment, the cavities 21 have a pyramidal shape or a conical shape. Therefore, the cells 40 are slid down along the slant surfaces of the pyramidal or conical cavities 21. Thus, the cells 40 can be condensed at a high density around the apex portions of the cavities 21.

Furthermore, according to the present embodiment, the ECM 41 is coated on the portions of the flat plate 32 which face the cavities 21. As the container 10*a* is inverted upside down, the cells 40 condensed inside the respective cavities 21 fall onto the portions on which the ECM 41 is coated. Thus, it is possible to carry out the culture of the cells 40 in situ.

Second Embodiment

Figure 3A:
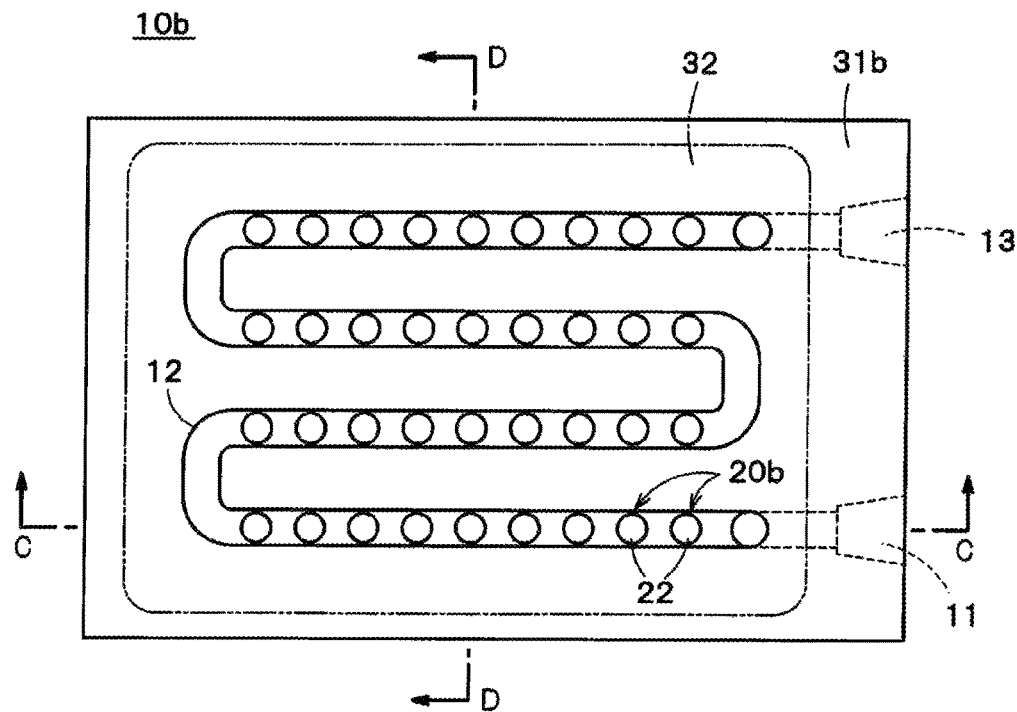
FIG. 3A is a schematic plane view illustrating a cell culture container according to a second embodiment of the present invention.
Figure 3B:
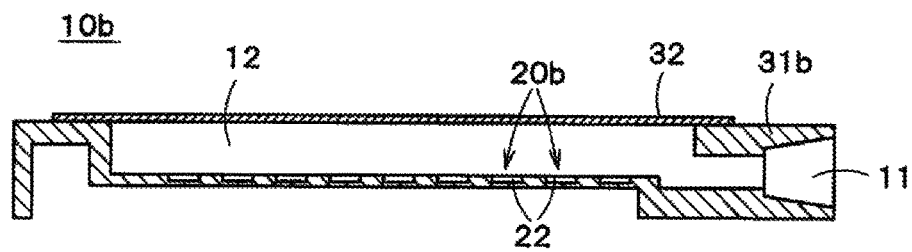
FIG. 3B is a sectional view of the cell culture container taken along line C-C in FIG. 3A.
Figure 3C:
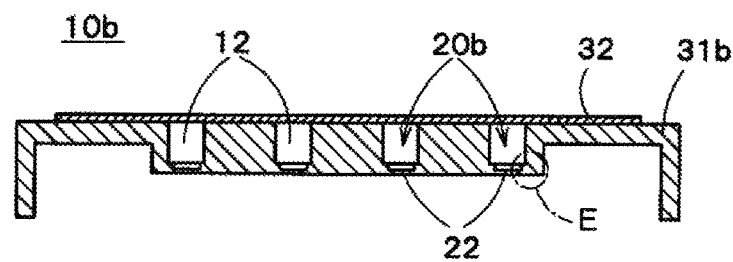
FIG. 3C is a sectional view of the cell culture container taken along line D-D in FIG. 3A.

Next, a second embodiment of the present invention will be described with reference to FIGS. 3A to 3C. FIG. 3A is a schematic plane view illustrating a cell culture container 10*b* according to a second embodiment of the present invention. FIG. 3B is a sectional view of the cell culture container 10*b* taken along line C-C in FIG. 3A. FIG. 3C is a sectional view of the cell culture container 10*b* taken along line D-D in FIG. 3A.

As illustrated in FIGS. 3A to 3C, in the cell culture container 10*b* according to the second embodiment, cavities 22 are formed on the bottom surface of the passage 12 in a concentric relationship with the cell-seeding areas 20*b*. Each of the cavities 22 has a flat bottom portion.

In the illustrated example, the cavities 22 have a circular shape in a plane view. However, the shape of the cavities 22 is not limited thereto but may be, for example, an elliptical shape or a polygonal shape in a plane view. The depth of the cavities 22 may be, for example, from 0.1 mm to 1.0 mm.

It is preferred that the thickness of the bottom portions of the cavities 22 is from 0.05 mm to 0.3 mm. As a result of actual verification conducted by the inventors using a silicone rubber membrane of hardness A30, if the bottom portions of the cavities 22 are thinner than 0.05 mm, the bottom portions of the cavities 22 are likely to be destroyed and the liquid leakage may possibly be generated.

Figure 4:
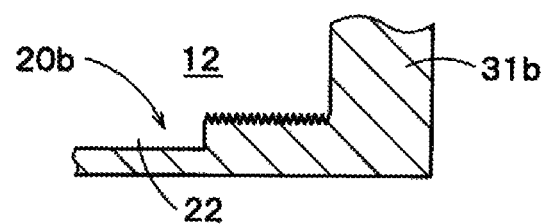
FIG. 4 is an enlarged schematic view of a portion surrounded by a single-dot chain line E in the cell culture container illustrated in FIG. 3C.

FIG. 4 is an enlarged schematic view of the portion surrounded by a single-dot chain line E in the cell culture container 10*b* illustrated in FIG. 3C.

As illustrated in FIG. 4, in the present embodiment, the outer surface roughness of the cell-seeding areas 20*b* (the cavities 22) is larger than the inner surface roughness of the cell-seeding areas 20*b* (the cavities 22). For example, the inner surface roughness of the cell-seeding areas 20*b* may be Ra 0.2 or less and the outer surface roughness of the cell-seeding areas 20*b* may be Ra 0.8 or less. The difference in the surface roughness can be realized by, for example, adjusting the surface roughness of a mold used in injection-molding the container main body 31*b*. As the outer surface roughness of the cell-seeding areas 20*b* (the cavities 22) grows larger, the cells are harder to adhere to the outside of the cell-seeding areas 20*b* (the cavities 22).

Other configurations of the second embodiment are substantially the same as the configurations of the first embodiment illustrated in FIGS. 1A to 1C. In FIGS. 3A to 3C and FIG. 4, the portions identical with those of the first embodiment illustrated in FIGS. 1A to 1C are designated by like reference symbols with the detailed descriptions thereof omitted.

Next, one example of a use method of the cell culture container 10*b* according to the second embodiment will be described with reference to FIGS. 5A to 5E.

Figure 5A:
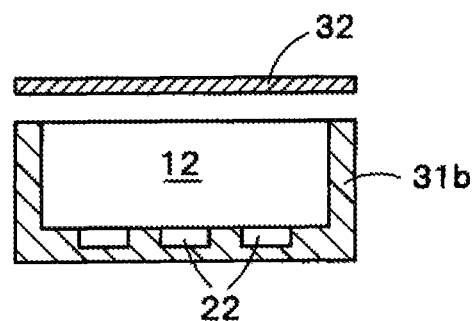
FIG. 5A is a schematic view for explaining one example of a use method of the cell culture container according to the second embodiment of the present invention.

First, as illustrated in FIG. 5A, the surface of the container main body 31*b*, on which the passage 12 is formed and to which the flat plate 32 is not yet attached, is processed by $O_2$ plasma. Specifically, for example, an $O_2$ gas supplied at a flow rate of 40 mL/min is converted to $O_2$ plasma by electric power of 27 kW. The surface of the container main body 31*b*, on which the passage 12 is formed, is exposed to the $O_2$ plasma for 5 minutes.

Then, a cell non-adhesive coating solution is coated on the passage 12 of the container main body 31*b*. Specifically, for example, 10 mL of the cell non-adhesive coating solution is allowed to flow into the passage 12 and is left at rest for 2 hours at 37° C. Thereafter, the cell non-adhesive coating solution is allowed to flow out from the passage 12. The passage 12 is cleaned with sterile water.

Figure 5B:
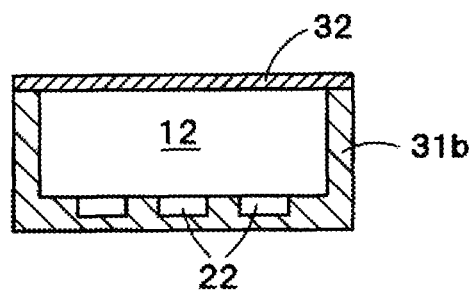
FIG. 5B is a schematic view for explaining one example of a use method of the cell culture container according to the second embodiment of the present invention.

Subsequently, as illustrated in FIG. 5B, the flat plate 32 is attached to one surface of the container main body 31*b*, on which the passage 12 is formed. Specifically, for example, an adhesive agent (not shown) is coated on the outer portion of the passage 12. Thereafter, the flat plate 32 is opposed to and placed on one surface of the container main body 31*b* so as to cover the entirety of the ceiling of the passage 12 and is bonded to one surface of the container main body 31*b* by an adhesive agent. Then, the adhesive agent is solidified at 40° C. for 16 hours by a drier.

Then, PBS is allowed to flow from the inflow port 11 into the passage 12. The passage 12 is filled with the PBS. Thus, air bubbles are removed from the passage 12. Thereafter, the culture container 10*b* is left at rest in such a posture that the container main body 31*b* is positioned under the flat plate 32.

Figure 5C:
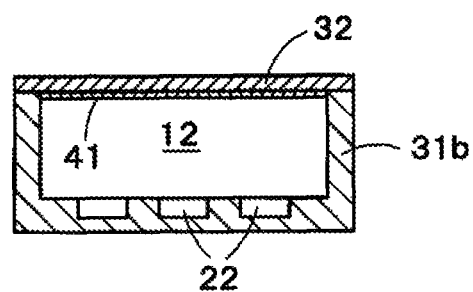
FIG. 5C is a schematic view for explaining one example of a use method of the cell culture container according to the second embodiment of the present invention.

Subsequently, as illustrated in FIG. 5C, an ECM 41 is coated on the region of the flat plate 32 that faces the cavities 22. Specifically, for example, 25 mL of the ECM (e.g., Vitronectin XF made by Stem Cell Technologies, Inc.) is allowed to flow from the inflow port 11 into the passage 12 in a state in which a 1 mL air plug is inserted into the inflow port 11. The PBS existing within the passage 12 is swept away by the ECM and is caused to flow out from the outflow port 13. In this state, the cell culture container 10*b* is left at rest for 1 hour. Thus, the ECM 41 adheres to the portion of the passage 12 on which the cell non-adhesive coating solution is not coated, namely the entire region of the flat plate 32 corresponding to the ceiling surface of the passage 12.

Figure 5D:
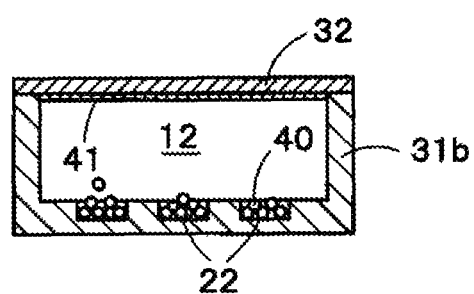
FIG. 5D is a schematic view for explaining one example of a use method of the cell culture container according to the second embodiment of the present invention.

Then, in a cell seeding process, as illustrated in FIG. 5D, 25 mL of a cell suspension in which cells 40 are dispersed (for example, a cell suspension in which WS cells are dispersed) is allowed to flow from the inflow port 11 into the passage 12 at a flow rate of, e.g., 1.0 mL/min to 20 mL/min, in a state in which a 1 mL air plug is inserted into the inflow port 11. The cells 40 in the cell suspension may be dispersed in the form of a single cell or in the form of a cell clump. The ECM not adhering to the flat plate 32 is swept away by the cell suspension and is caused to flow out from the outflow port 13.

In the present embodiment, the orientation of the liquid flow from the inflow port 11 to the outflow port 13 is limited by the passage 12. Therefore, within the passage 12, the moving direction of individual liquid molecules constituting the liquid is aligned parallel to the passage 12. That is to say, occurrence of a turbulent flow between the inflow port 11 and the outflow port 13 is suppressed. Thus, occurrence of unevenness of a cell density in the cell suspension suppressed. The cells 40 are controlled to fall (precipitate) onto the bottom surface of the passage 12 at a practically-permissible uniform density.

Furthermore, in the present embodiment, the outer surface roughness of the cell-seeding areas 20b is relatively large. Therefore, adhesion of the cells to the outside of the cell-seeding areas 20b is suppressed.

Subsequently, vibration (of a frequency of, e.g., 180 Hz) is applied to the entirety of the cell culture container 10b for 30 minutes. Thus, the cells 40 falling onto the outside of the cavities 22 of the bottom surface of the passage 12 are guided into the cavities 22. That is to say, the cells 40 are effectively seeded inside the cell-seeding areas 20b. Specifically, for example, about 500 to 5000 cells 40 are seeded within each of the cavities 22.

Instead of applying vibration to the entirety of the cell culture container 10bZ or in addition to applying vibration to the entirety of the cell culture container 10b, the cell culture container 10b as a whole may be tilted so that one side (e.g., the right side in FIG. 3A) of the cell culture container 10b becomes lower than the other side (e.g., the left side in FIG. 3A) of the cell culture container 10b. In this case, the cells 40 falling onto the bottom surface of the passage 12 are slid down toward one side of the cell culture container 10b along the slant surface. Thus, the cells 40 can be condensed at a high density in one side (right side) edge of the interior of the cavities 22.

Figure 5E:
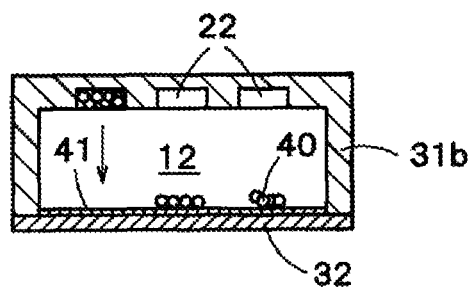
FIG. 5E is a schematic view for explaining one example of a use method of the cell culture container according to the second embodiment of the present invention.

Subsequently, as illustrated in FIG. 5E, the cell culture container 10b is inverted upside down after it is left at rest. Thus, the cells 40 condensed inside the cavities 22 fall onto the portions of the flat plate 32 which face the cavities 22.

Since the ECM 41 is coated on the portions of the flat plate 32 which face the cavities 22, the cells 40 falling onto the flat plate 32 can be cultured in situ using the ECM 41 as a scaffold.

Subsequently, after the cell culture container 10b is left at rest for 48 hours, the cultured cells 40 are optically observed from the outside.

Then, in a medium exchange process, a medium (e.g., ReproFF2 made by Reprocell, Inc.) is allowed to flow from the inflow port 11 into the passage 12 at a flow rate of, for example, 10 mL/min to 20 mL/min. The old medium existing within the passage 12 is swept away by the new medium and is allowed to flow out from the outflow port 13. In the present embodiment, a flow moving along the passage 12 is formed within the passage 12. For that reason, the new medium is hardly mixed with the old medium. Since the old medium is swept away by the new medium, it is possible to easily and effectively exchange the old medium with the new medium without continuously supplying the new medium.

Then, after the cell culture container 10b is left at rest for 48 hours, the cultured cells 40 are optically observed from the outside.

Subsequently, in a medium exchange process, a medium (e.g., ReproFF2 made by Reprocell, Inc.) is allowed to flow from the inflow port 11 into the passage 12 at a flow rate of, for example, 10 mL/min to 20 mL/min. The old medium existing within the passage 12 is swept away by the new medium and is allowed to flow out from the outflow port 13.

Thereafter, the cell culture container 10b is further left at rest for 48 hours. Thus, the cells 40 are cultured until the number of cells 40 becomes equal to 3000 to 20000 per one colony.

Subsequently, in a cell recovery process, a release agent (for example, TrypLE Select made by Life technologies, Inc.) is allowed to flow from the inflow port 11 into the passage 12 at a flow rate of, for example, 10 mL/min to 20 mL/min. The old medium existing within the passage 12 is swept away by the release agent and is allowed to flow out from the outflow port 13. The colonies of the cells 40 cultured on the flat plate 32 are separated from the ECM 41 by the release agent.

Thereafter, a medium (e.g., ReproFF2 made by Reprocell, Inc.) is allowed to flow from the inflow port 11 into the passage 12 at a flow rate of, for example, 10 mL/min to 20 mL/min. The colonies of the cultured cells 40 separated from the ECM 41 are swept away by the new medium and are allowed to flow out (recovered) from the outflow port 13. In the present embodiment, a flow moving along the passage 12 is formed within the passage 12. Therefore, a shear stress is applied uniformly to the bottom surface of the passage 12. This reduces missing of the cultured cells 40.

Next, another example of a use method of the cell culture container 10b according to the second embodiment will be described with reference to FIGS. 6A to 6C.

Figure 6A:
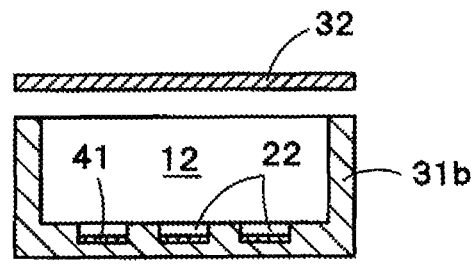
FIG. 6A is a schematic view for explaining another example of a use method of the cell culture container according to the second embodiment of the present invention.

First, as illustrated in FIG. 6A, in the container main body 31b to which the flat plate 32 is not yet attached, the ECM 41 is coated inside the cavities 22. However, the ECM 41 is not coated outside the cavities 22. Specifically, for example, Vitronectin XF made by Stem Cell Technologies, Inc. as the ECM is dropped on only the inside of the cavities 22 of the container main body 31b by a droplet dropping device or the like. Thereafter, the dropped ECM 41 is dried. Thus, the consumption amount of the ECM 41 is sharply reduced (For example, the consumption amount of the ECM 41 is 1 mL or less).

Figure 6B:
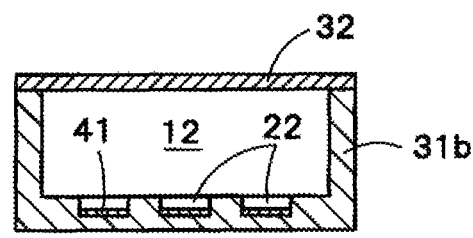
FIG. 6B is a schematic view for explaining another example of a use method of the cell culture container according to the second embodiment of the present invention.

Then, as illustrated in FIG. 6B, the flat plate 32 is attached to one surface of the container main body 31b, on which the passage 12 is formed. Specifically, for example, an adhesive agent (not shown) is coated on the outer portion of the passage 12. Thereafter, the flat plate 32 is opposed to and placed on one surface of the container main body 31b so as to cover the entirety of the ceiling of the passage 12 and is bonded to one surface of the container main body 31b by an adhesive agent. Then, the adhesive agent is solidified at 40° C. for 16 hours by a drier.

Then, PBS is allowed to flow from the inflow port 11 into the passage 12. The passage 12 is filled with the PBS. Thus, air bubbles are removed from the passage 12. Thereafter, the culture container 10b is left at rest in such a posture that the container main body 31b is positioned under the flat plate 32.

Figure 6C:
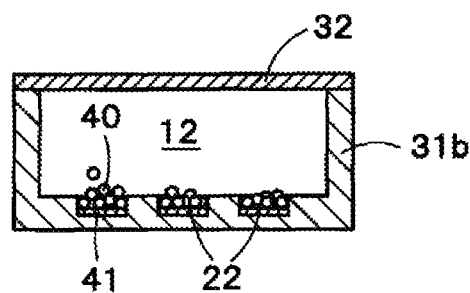
FIG. 6C is a schematic view for explaining another example of a use method of the cell culture container according to the second embodiment of the present invention.

Subsequently, in a cell seeding process, as illustrated in FIG. 6C, 25 mL of a cell suspension in which cells 40 are dispersed (for example, a cell suspension in which iPS cells are dispersed) is allowed to flow from the inflow port 11 into the passage 12 at a flow rate of, e.g., 10 mL/min to 20 mL/min, in a state in which a 1 mL air plug is inserted into the inflow port 11. The cells 40 in the cell suspension may be dispersed in the form of a single cell or in the form of a cell clump. The PBS existing in the passage 12 is swept away by the cell suspension and is caused to flow out from the outflow port 13.

In the present embodiment, the orientation of the liquid flow from the inflow port 11 to the outflow port 13 is limited by the passage 12. Therefore, within the passage 12, the moving direction of individual liquid molecules constituting the liquid is aligned parallel to the passage 12. That is to say, occurrence of a turbulent flow between the inflow port 11 and the outflow port 13 is suppressed. Thus occurrence of unevenness of a cell density in the cell suspension is suppressed. The cells 40 are controlled to fall (precipitate) onto the bottom surface of the passage 12 at a practically-permissible uniform density.

Furthermore, in the present embodiment, the outer surface roughness of the cell-seeding areas 20*b* is relatively large. Therefore, adhesion of the cells to the outside of the cell-seeding areas 20*b* is suppressed.

Subsequently, vibration (of a frequency of, e.g., 180 Hz) is applied to the entirety of the cell culture container 10*b* for 30 minutes. Thus, the cells 40 falling onto the outside of the cavities 22 of the bottom surface of the passage 12 are guided into the cavities 22. That is to say, the cells 40 are effectively seeded inside the cell-seeding areas 20*b*. Specifically, for example, about 500 to 1000 cells 40 are seeded within each of the cavities 22.

Instead of applying vibration to the entirety of the cell culture container 10*b* or in addition to applying vibration to the entirety of the cell culture container 10*b*, the cell culture container 10*b* as a whole may be tilted so that one side (e.g., the right side in FIG. 3A) of the cell culture container 10*b* becomes lower than the other side (e.g., the left side in FIG. 3A) of the cell culture container 10*b*. In this case, the cells 40 falling onto the bottom surface of the passage 12 are slid down toward one side of the cell culture container 10*b* along the slant surface. Thus, the cells 40 can be condensed at a high density in one side (right side) edge of the interior of the cavities 22.

As illustrated in FIG. 6C, the ECM 41 is coated inside the cavities 22. Therefore, the cells 40 seeded inside the cavities 22 can be cultured in situ using the ECM 41 as a scaffold.

Subsequently, after the cell culture container 10*b* is left at rest for 48 hours, the cultured cells are optically observed.

Then, in a medium exchange process, a medium (e.g., ReproFF2 made by Reprocell, Inc.) is allowed to flow from the inflow port 11 into the passage 12 at a flow rate of, for example, 10 mL/min to 20 mL/min. The old medium existing within the passage 12 is swept away by the new medium and is allowed to flow out from the outflow port 13. In the present embodiment, a flow moving along the passage 12 is formed within the passage 12. For that reason, the new medium is hardly mixed with the old medium. Since the old medium is swept away by the new medium, it is possible to easily remove the old medium without continuously supplying the new medium and to effectively exchange the old medium with the new medium.

Then, after the cell culture container 10*b* is left at rest for 48 hours, the cultured cells are optically observed.

Subsequently, in a medium exchange process, a medium (e.g., ReproFF2 made by Reprocell, Inc.) is allowed to flow from the inflow port 11 into the passage 12 at a flow rate of, for example, 10 mL/min to 20 mL/min. The old medium existing within the passage 12 is swept away by the new medium and is allowed to flow out from the outflow port 13.

Thereafter, the cell culture container 10*b* is further left at rest for 48 hours. The cells 40 are cultured until the number of cells 40 becomes equal to 10000 to 20000 per one colony.

Subsequently, in a cell recovery process, a release agent (for example, TrypLE Select made by Life technologies, Inc.) is allowed to flow from the inflow port 11 into the passage 12 at a flow rate of, for example, 10 mL/min to 20 mL/min. The old medium existing within the passage 12 is swept away by the release agent and is allowed to flow out from the outflow port 13. The colonies of the cells 40 cultured in the cavities 22 are separated from the ECM 41 by the release agent.

Thereafter, a medium (e.g., ReproFF2 made by Reprocell, Inc.) is allowed to flow from the inflow port 11 into the passage 12 at a flow rate of, for example, 10 mL/min to 20 mL/min. The colonies of the cultured cells 40 separated from the ECM 41 are swept away by the new medium and are allowed to flow out (recovered) from the outflow port 13. In the present embodiment, a flow moving along the passage 12 is formed within the passage 12. Therefore, a shear stress is applied uniformly to the bottom surface of the passage 12. This reduces missing of the cultured cells 40.

According to the present embodiment described above, as illustrated in FIGS. 6A to 6C, if the ECM 41 is coated inside the cavities 22 and is not coated outside the cavities 22, the culture can be carried out in situ without inverting the container upside down after the cells are seeded inside the cavities 22. Since the ECM 41 are not coated outside the cavities 22, it is possible to sharply reduce the consumption amount of the ECM and to effectively control the culture positions of the cells 40 to the inside of the cavities 22.

Third Embodiment

Figure 7A:
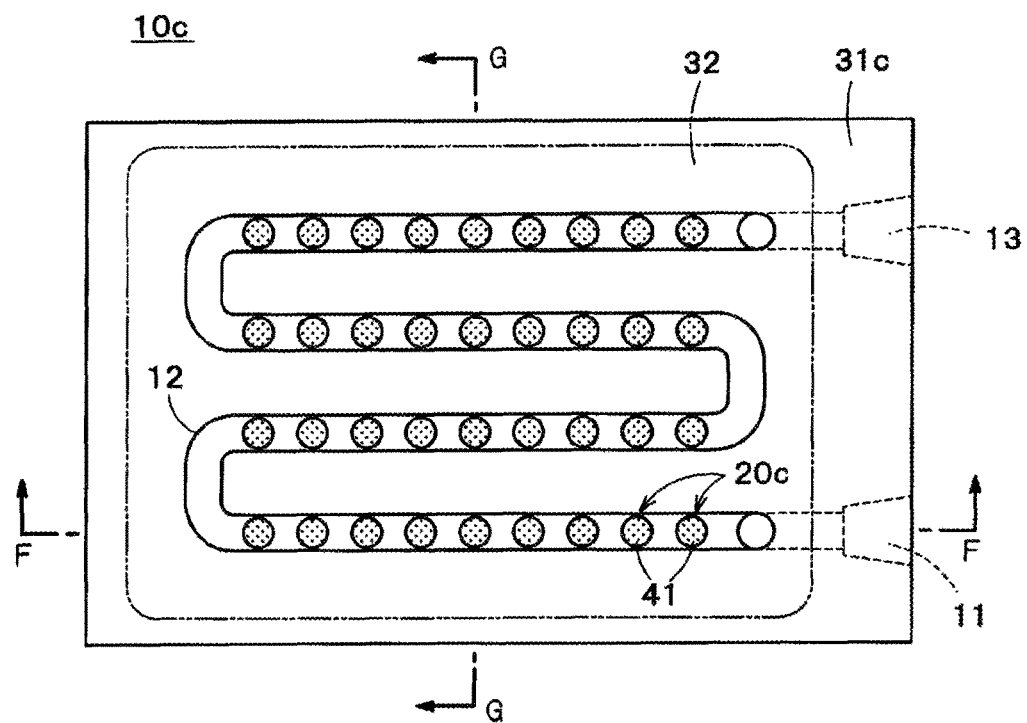
FIG. 7A is a schematic plane view illustrating a cell culture container according to a third embodiment of the present invention.
Figure 7B:
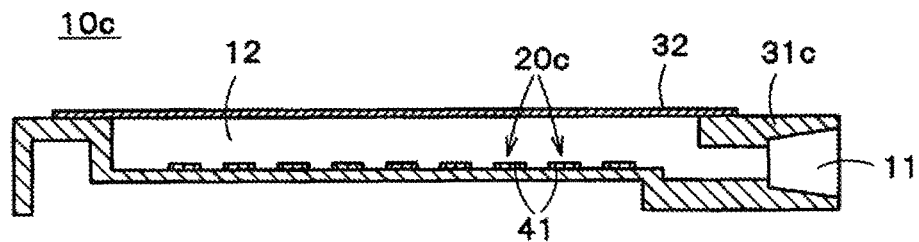
FIG. 7B is a sectional view of the cell culture container taken along line F-F in FIG. 7A.
Figure 7C:
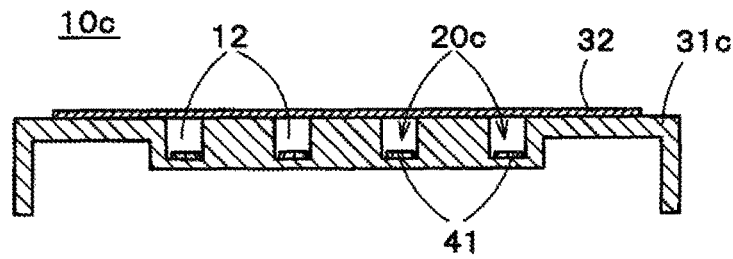
FIG. 7C is a sectional view of the cell culture container taken along line G-G in FIG. 7A.

Next, a third embodiment of the present invention will be described with reference to FIGS. 7A to 7C. FIG. 7A is a schematic plane view illustrating a cell culture container 10*c* according to a third embodiment of the present invention. FIG. 7B is a sectional view of the cell culture container 10*c* taken along line F-F in FIG. 7A. FIG. 7C is a sectional view of the cell culture container 10*c* taken along line G-G in FIG. 7A.

As illustrated in FIGS. 7A to 7C, in the cell culture container 10*c* according to the third embodiment, the bottom surface of the passage 12 is flat. The ECM 41 is coated inside the cell-seeding areas 20*c* arranged side by side along the passage 12. The ECM 41 is not coated outside the cell-seeding areas 20*c*. Descriptions will be made on a method of coating the ECM 41. For example, Vitronectin XF made by Stem Cell Technologies, Inc. as the ECM is dropped on only the inside of the cell-seeding areas 20*c* of the bottom surface of the passage 12 by a droplet dropping device or the like. Thereafter, the dropped ECM 41 is dried. It is therefore possible to sharply reduce the consumption amount of the ECM and to effectively control the culture positions of the cells to the inside of the cell-seeding areas 20*c*.

While not shown in the drawings, the outer surface roughness of the cell-seeding areas 20*c* is larger than the inner surface roughness of the cell-seeding areas 20*c*. For example, the inner surface roughness of the cell-seeding areas 20*c* may be Ra 0.2 or less and the outer surface roughness of the cell-seeding areas 20*c* may be Ra 0.8 or less. The difference in the surface roughness can be realized by, for example, adjusting the surface roughness of a mold used in injection-molding the container main body 31*c*. As the outer surface roughness of the cell-seeding areas 20c grows larger, the cells are harder to adhere to the outside of the cell-seeding areas 20c.

Other configurations of the third embodiment are substantially the same as the configurations of the second embodiment illustrated in FIGS. 3A to 3C. In FIGS. 7A to 7C, the portions identical with those of the second embodiment illustrated in FIGS. 3A to 3C are designated by like reference symbols with the detailed descriptions thereof omitted.

Next, one example of a use method of the cell culture container 10c according to the third embodiment will be described with reference to FIGS. 8A to 8C.

Figure 8A:
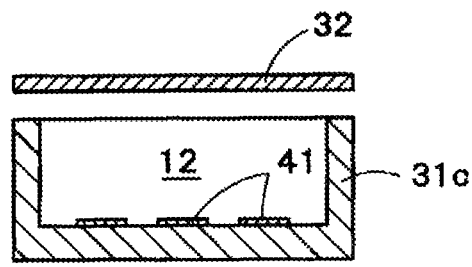
FIG. 8A is a schematic view for explaining one example of a use method of the cell culture container according to the third embodiment of the present invention.

As illustrated in FIG. 8A, in the container main body 31c to which the flat plate 32 is not yet attached, the ECM 41 is previously coated on the cell-seeding areas 20c arranged side by side along the passage 12. The ECM 41 is not coated outside the cell-seeding areas 20c.

Figure 8B:
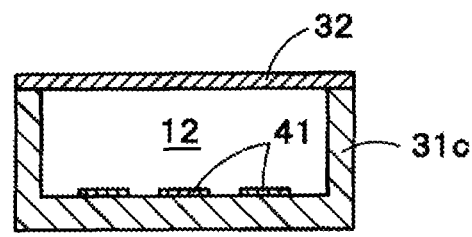
FIG. 8B is a schematic view for explaining one example of a use method of the cell culture container according to the third embodiment of the present invention.

First, as illustrated in FIG. 8B, the flat plate 32 is attached to one surface of the container main body 31c, on which the passage 12 is formed. Specifically, for example, an adhesive agent (not shown) is coated on the outer portion of the passage 12. Thereafter, the flat plate 32 is opposed to and placed on one surface of the container main body 31c so as to cover the entirety of the ceiling of the passage 12 and is bonded to one surface of the container main body 31c by an adhesive agent. Then, the adhesive agent is solidified at 40° C. for 16 hours by a drier.

Then, PBS is allowed to flow from the inflow port 11 into the passage 12. The passage 12 is filled with the PBS. Thus, air bubbles are removed from the passage 12. Thereafter, the culture container 10c is left at rest in such a posture that the container main body 31c is positioned under the flat plate 32.

Figure 8C:
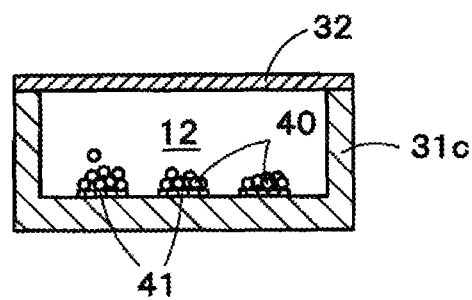
FIG. 8C is a schematic view for explaining one example of a use method of the cell culture container according to the third embodiment of the present invention.

Subsequently, in a cell seeding process, as illustrated in FIG. 8C, 25 mL of a cell suspension in which cells 40 are dispersed (for example, a cell suspension in which iPS cells are dispersed) is allowed to flow from the inflow port 11 into the passage 12 at a flow rate of, e.g., 10 mL/min to 20 mL/min, in a state in which a 1 mL air plug is inserted into the inflow port 11. The cells 40 in the cell suspension may be dispersed in the form of a single cell or in the form of a cell clump. The PBS existing in the passage 12 is swept away by the cell suspension and is caused to flow out from the outflow port 13.

In the present embodiment, the orientation of the liquid flow from the inflow port 11 to the outflow port 13 is limited by the passage 12. Therefore, within the passage 12, the moving direction of individual liquid molecules constituting the liquid is aligned parallel to the passage 12. That is to say, occurrence of a turbulent flow between the inflow port 11 and the outflow port 13 is suppressed. Thus occurrence of unevenness of a cell density in the cell suspension is suppressed. The cells 40 are controlled to fall (precipitate) onto the bottom surface of the passage 12 at a practically-permissible uniform density.

In the present embodiment, the ECM 41 is coated inside the cell-seeding areas 20c. However, the ECM 41 is not coated outside the cell-seeding areas 20c. Therefore, adhesion of the cells to the outside of the cell-seeding areas 20c is suppressed. Thus, the cells 40 are effectively seeded inside the cell-seeding areas 20c. Specifically, for example, about 500 to 5000 cells 40 are seeded within each of the cell-seeding areas 20c.

Since the ECM 41 is coated inside the cell-seeding areas 20c, the cells 40 condensed inside the cell-seeding areas 20c can be cultured in situ using the ECM 41 as a scaffold.

Subsequently, after the cell culture container 10c is left at rest for 48 hours, the cultured cells 40 are optically observed from the outside.

Then, in a medium exchange process, a medium (e.g., ReproFF2 made by Reprocell, Inc.) is allowed to flow from the inflow port 11 into the passage 12 at a flow rate of, for example, 10 mL/min to 20 mL/min. The old medium existing within the passage 12 is swept away by the new medium and is allowed to flow out from the outflow port 13. In the present embodiment, a flow moving along the passage 12 is formed within the passage 12. For that reason, the new medium is hardly mixed with the old medium. Since the old medium is swept away by the new medium, it is possible to easily remove the old medium without continuously supplying the new medium and to effectively exchange the old medium with the new medium.

Subsequently, after the cell culture container 10c is further left at rest for 48 hours, the cultured cells 40 are optically observed from the outside.

Subsequently, in a medium exchange process, a medium (e.g., ReproFF2 made by Reprocell, Inc.) is allowed to flow from the inflow port 11 into the passage 12 at a flow rate of, for example, 10 mL/min to 20 mL/min. The old medium existing within the passage 12 is swept away by the new medium and is allowed to flow out from the outflow port 13.

Thereafter, the cell culture container 10c is further left at rest for 48 hours. Thus, the cells 40 are cultured until the number of cells 40 becomes equal to 10000 to 20000 per one colony.

Subsequently, in a cell recovery process, a release agent (for example, TrypLE Select made by Life technologies, Inc.) is allowed to flow from the inflow port 11 into the passage 12 at a flow rate of, for example, 10 mL/min to 20 mL/min. The old medium existing within the passage 12 is swept away by the release agent and is allowed to flow out from the outflow port 13. The colonies of the cells 40 cultured on the bottom surface of the passage 12 are separated from the ECM 41 by the release agent.

Thereafter, a medium (e.g., ReproFF2 made by Reprocell, Inc.) is allowed to flow from the inflow port 11 into the passage 12 at a flow rate of, for example, 10 mL/min to 20 mL/min. The colonies of the cultured cells 40 separated from the ECM 41 are swept away by the new medium and are allowed to flow out (recovered) from the outflow port 13. In the present embodiment, a flow moving along the passage 12 is formed within the passage 12. Therefore, a shear stress is applied uniformly to the bottom surface of the passage 12. This reduces missing of the cultured cells 40.

According to the third embodiment described above, the ECM 41 is not coated outside the cell-seeding areas 20c. It is therefore possible to sharply reduce the consumption amount of the ECM and to effectively control the culture positions of the cells 40 to the inside of the cell-seeding areas 20c.

Furthermore, according to the present embodiment, the bottom surface of the passage 12 is flat. Therefore, the visibility of the cells 40 in culture is good.

Fourth Embodiment

Next, a fourth embodiment of the present invention will be described with reference to FIG. 9. FIG. 9 is a schematic plane view illustrating a cell culture container 10d according to a fourth embodiment of the present invention.

As illustrated in FIG. 9, in the cell culture container 10d according to the fourth embodiment, the passage 12' includes a branching section 129a in which the passage 12' is branched into a plurality of (eight, in the illustrated example) passage components 121 to 128 and a merging section 129b in which the passage components 121 to 128 are merged. From the viewpoint of uniformly aligning the conductance of the respective passage components 121 to 128, it is preferred that each of the branching section 129a and the merging section 129b has a tree shape as shown, namely a shape in which two branches are repeated n times and are uniformly branched into n passage components.

The cell-seeding areas 20d of the present embodiment are disposed on the bottom surfaces of the respective passage components 121 to 128 and are arranged side by side along the passage components 121 to 128.

When passing through the passage 12', the liquid flowing into the passage 12' from the inflow port 11 is branched into the respective passage components 121 to 128 in the branching section 129a. The liquid passing through the respective passage components 121 to 128 is merged in the merging section 129b and is guided to the outflow port 13. In this way, the orientation of the liquid flow from the inflow port 11 to the outflow port 13 is limited by the respective passage components of the passage 12'. Therefore, within the passage 12, the moving direction of individual liquid molecules constituting the liquid is aligned parallel to the passage 12. That is to say, occurrence of a turbulent flow between the inflow port 11 and the outflow port 13 is suppressed.

Other configurations of the fourth embodiment are substantially the same as the configurations of the first embodiment illustrated in FIGS. 1A to 1C. In FIG. 9, the portions identical with those of the first embodiment illustrated in FIGS. 1A to 1C are designated by like reference symbols with the detailed descriptions thereof omitted.

Furthermore, the use method of the cell culture container 10d according to the fourth embodiment is substantially the same as the use method of the cell culture container 10a according to the first embodiment. Detailed descriptions thereof are omitted.

According to the fourth embodiment described above, it is possible to extend the total length of the passage 12' without increasing the size of the container main body 31d. This makes it possible to increase the number of culture positions without enlarging the width of the passage 12'. Consequently, a larger number of cell clumps can be simultaneously cultured in one container 10d.

Furthermore, in the present embodiment, as illustrated in FIG. 9, the cavities 21a are formed on the bottom surface of the passage 12' in a concentric relationship with the cell-seeding areas 20d. The cavities 21a have a pyramidal shape or conical shape (a quadrangular pyramid shape in the illustrated example). However, the shape of the cavities 21a is not limited thereto. For example, similar to the second embodiment, cavities may be formed on the bottom surface of the passage 12' in a concentric relationship with the cell-seeding areas 20d. Each of the cavities may have a flat bottom portion. Alternatively, similar to the third embodiment, the bottom surface of the passage 12' may be flat. An ECM may be coated inside the cell-seeding areas 20d and may not be coated outside the cell-seeding areas 20d.

The invention disclosed herein is not limited by the respective embodiments described above. The respective embodiments may be appropriately combined unless a conflict arises in the process content.

EXPLANATION OF REFERENCE NUMERALS

10a: cell culture container, 10b: cell culture container, 10c: cell culture container, 10d: cell culture container, 11: inflow port, 12: passage, 12': passage, 121: passage component, 122: passage component, 123: passage component, 124: passage component, 125: passage component, 126: passage component, 127: passage component, 128: passage component, 129a: branching section, 129b: merging section, 13: outflow port, 20a: cell-seeding area, 20b: cell-seeding area, 20c: cell-seeding area, 20d: cell-seeding area, 21: depression, 22: depression, 31a: container main body, 31b: container main body, 31c: container main body, 31d: container main body, 32: flat plate, 40: cell, 41: extracellular matrix (ECM)

What is claimed is:

1. A cell culture container, comprising:
   a container main body; and
   a flat plate attached to one surface of the container main body,
   wherein the container main body includes an inflow port through which a liquid flows into the container main body, a passage through which the liquid flowing into the container main body from the inflow port passes, and an outflow port through which the liquid passing through the passage flows out from the container main body,
   wherein a plurality of cell-seeding areas, in which cells passing through the passage are seeded, is provided on a bottom surface of the passage, the cell-seeding areas arranged side by side along the passage,
   wherein the passage is uniform and is formed in a groove shape,
   wherein cavities are formed on the bottom surface of the passage in a concentric relationship with the cell-seeding areas, and
   wherein an extracellular matrix (ECM) is coated on a portion of the flat plate that faces the cavities, or is coated inside the cavities and is not coated outside the cavities.

2. The container of claim 1, wherein a ratio of width and length of the passage is set such that the width:the length is equal to 3:60 to 1800.

3. The container of claim 1, wherein the flat plate is fixedly supported by a tip region of a wall that defines the passage.

4. The container of claim 1, wherein
   the cell-seeding areas are provided at regular intervals along the passage.

5. The container of claim 1, wherein the passage includes a serpentine portion.

6. The container of claim 1, wherein the passage includes a branching section in which the passage is branched into a plurality of passage components and a merging section in which the passage components are merged.

7. The container of claim 1, wherein the cavities have a pyramidal shape or a conical shape.

8. The container of claim 1, wherein each of the cavities includes a flat bottom portion.

9. The container of claim 4, wherein the bottom surface of the passage is flat and the ECM is coated inside the cell-seeding areas and is not coated outside the cell-seeding areas.

10. The container of claim 4, wherein a surface roughness of the bottom surface of the passage is larger than a surface roughness of the cell-seeding areas.

11. The container of claim 1, wherein the bottom surface of the passage and the flat plate have optical transparency.

12. The container of claim 1, wherein the flat plate has gas permeability.

\* \* \* \* \*

UNITED STATES PATENT AND TRADEMARK OFFICE
CERTIFICATE OF CORRECTION

PATENT NO. : 10,351,811 B2  
APPLICATION NO. : 15/240284  
DATED : July 16, 2019  
INVENTOR(S) : Tomoaki Kurakazu et al.

Page 1 of 1

It is certified that error appears in the above-identified patent and that said Letters Patent is hereby corrected as shown below:

On the Title Page

In item (71) Applicant, please delete "SINFONIA TECHNOLOGY CO., LT." and replace with "SINFONIA TECHNOLOGY CO., LTD."

Signed and Sealed this  
Tenth Day of September, 2019

Andrei Iancu  
*Director of the United States Patent and Trademark Office*